(12) United States Patent
Stamler et al.

(10) Patent No.: US 6,314,956 B1
(45) Date of Patent: Nov. 13, 2001

(54) PULMONARY DELIVERY OF NO GROUP-CONTAINING COMPOUND IN GAS FORM TO TREAT RESPIRATORY, CARDIAC AND BLOOD DISORDERS

(75) Inventors: Jonathan S. Stamler, Chapel Hill; Eric J. Toone; Andrew J. Gow, both of Durham, all of NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/390,215

(22) Filed: Sep. 8, 1999

(51) Int. Cl.$^7$ .................. A61M 15/00; A61M 16/00; A62B 18/00; A62B 7/00; A62B 9/00
(52) U.S. Cl. ................................ 128/200.24
(58) Field of Search ............... 128/200.14, 200.23, 128/200.24, 203.12, 203.16, 203.17, 203.22, 203.26, 203.27

(56) References Cited

U.S. PATENT DOCUMENTS

| | | | |
|---|---|---|---|
| 4,353,843 | 10/1982 | Doumaux, Jr. et al. | 558/488 |
| 4,908,466 | 3/1990 | Nelson | 558/488 |
| 5,278,192 | 1/1994 | Fung et al. | 514/645 |
| 5,412,147 | 5/1995 | Landscheidt et al. | 558/488 |
| 5,485,827 | 1/1996 | Zapol et al. | 128/200.14 |
| 5,489,610 | 2/1996 | Fung et al. | 514/506 |
| 5,570,683 * | 11/1996 | Zapol et al. | 128/203.12 |
| 5,571,524 | 11/1996 | Kitakaze et al. | 424/423 |
| 5,583,101 | 12/1996 | Stamler et al. | 514/2 |
| 5,649,322 | 7/1997 | Landscheidt et al. | 558/488 |
| 5,713,349 | 2/1998 | Keaney | 128/204.23 |
| 5,770,645 | 6/1998 | Stamler et al. | 524/419 |
| 5,823,180 | 10/1998 | Zapol | 128/200.24 |
| 5,824,669 | 10/1998 | Garvey et al. | 514/174 |
| 5,863,890 | 1/1999 | Stamler et al. | 514/2 |
| 5,873,359 * | 2/1999 | Zapol et al. | 128/203.12 |
| 5,958,427 | 9/1999 | Salzman et al. | 424/406 |

OTHER PUBLICATIONS

The Merck Index, 12$^{th}$ Edition, 1996, Merck & Co., Inc., Whitehouse Station, N.J., p. 651, Item 3877.

* cited by examiner

Primary Examiner—John G. Weiss
Assistant Examiner—Joseph F. Weiss, Jr.

(57) ABSTRACT

Treatment of pulmonary disorders associated with hypoxemia and/or smooth muscle constriction comprises administering into the lungs as a gas a compound with an NO group which does not form $NO_2/NO_x$ in the presence of oxygen or reactive oxygen species at body temperature. Treatment of cardiac and blood disorders, e.g., angina, myocardial infarction, heart failure, hypertension, sickle cell disease and clotting disorders, comprises administering into the lungs as a gas, a compound which reacts with cysteine in hemoglobin and/or dissolves in blood and has an NO group which is bound in said compound so that it does not form $NO_2/NO_x$ in the presence of oxygen or reactive oxygen species at body temperature. Exemplary of the compound administered in each case is ethyl nitrite.

22 Claims, 7 Drawing Sheets

PULMONARY DELIVERY OF NO GROUP-CONTAINING COMPOUND IN GAS FORM TO TREAT RESPIRATORY, CARDIAC AND BLOOD DISORDERS

TECHNICAL FIELD

This invention relates to the treatment of respiratory, cardiac and blood disorders by delivery into the lungs of compound comprising NO.

BACKGROUND OF THE INVENTION

Inhaled NO is used to treat elevated pulmonary pressures and pulmonary disorders associated with hypoxemia. This method of treatment provides distribution tightly matched to perfusion and local effect because of rapid trapping of inhaled NO by hemoglobin. Moreover, this method of treatment can be readily carried out by an anesthesiologist or a critical care physician who is used to administering gases. Side effects include reaction of NO with oxygen or reactive oxygen species to produce $NO_2$ or other toxic $NO_x$, the toxicity of which is manifested by inflammation, airway hyperactivity, hemorrhage or delay in clinical improvement, and reaction with oxyhemoglobin to interfere with its oxygen delivery function, e.g., by forming methemoglobin.

An alternative to inhaled NO gas is nebulized NO donor where the NO donor is present as solid particles or as particles of liquid. This alternative cannot fully avoid the $NO_2/NO_x$ toxicity problem associated with administration of NO but may produce longer lasting effects than inhaled NO. The distribution in the lungs is according to particle size and is not matched to perfusion so some NO donor deposits in places where it does not reach the blood. Furthermore, this method is not as readily carried out by an anesthesiologist since anesthesiologists do not normally administer aerosols or powders. Moreover, some classes of NO donors have additional toxicities, that is, they possess toxicities that are unrelated to NO, but that are instead related to the group to which NO is attached or from which NO is generated. The disadvantages of administering nebulized NO donor are indicated to be meaningful by the fact that inhaled gaseous NO is approved for use over inhaled liquid or inhaled solid NO-releasing compound.

Use of inhaled NO and use of nitric oxide-releasing compounds inhaled as solids or liquids in an aerosol to treat pulmonary vasoconstriction and asthma are described in Zapol U.S. Pat. No. 5,823,180.

SUMMARY OF THE INVENTION

It is an object of an embodiment herein to provide selective pulmonary vasodilation and hypoxemia relieving effect by administration to the lungs of a gas without the toxicity associated with NO use.

It is an object of an embodiment herein to systemically deliver NO/SNO by administering into the lungs of a gas without interfering with the oxygen delivery function of hemoglobin. It also is an object of this embodiment to endow hemoglobin with improved and/or novel NO donor/releasing function.

It is an additional object to deliver NO/SNO without the toxicity (loss of specificity) associated with certain classes of NO donors.

One embodiment herein is directed to a method for treating a pulmonary disorder associated with hypoxemia and/or smooth muscle constriction in a patient having such disorder, said method comprising delivering into the lungs of said patient as a gas, a therapeutically effective amount of a compound having an NO group and having a hypoxemia relieving and smooth muscle constriction relieving effect with said NO group being bound in said compound so it does not form $NO_2$ or $NO_x$ in the presence of oxygen or reactive oxygen species at body temperature.

Another embodiment herein is directed at a method of treating a cardiac disorder which is characterized by ischemia, pump failure and/or afterload increase in a patient having such disorder, said method comprising delivering into the lungs of said patient as a gas, a therapeutically effective amount of a compound which reacts with cysteine in hemoglobin and/or dissolves in blood and has an NO group which is bound in said compound so it does not form $NO_2$ or $NO_x$ in the presence of oxygen or reactive oxygen species at body temperature, whereby delivering into the lungs causes a systemic effect.

Still another embodiment herein is directed at a method of treating a blood disorder which is ameliorated by treatment with NO in a patient having said disorder, said method comprising delivering into the lungs of said patient as a gas, a therapeutically effective amount of a compound which reacts with cysteine in hemoglobin and/or dissolves in blood and has an NO group which is bound in said compound so that it does not form $NO_2$ or $NO_x$ in the presence of oxygen or reactive oxygen species at body temperature, whereby delivery into the lungs causes a systemic effect.

Exemplary of compound useful in each of the embodiments is ethyl nitrite.

Advantages of embodiments herein include: (1), elimination of the toxicity caused by $NO_2/NO_x$ formation; (2), the option of administering the compound comprising NO group together with oxygen, without $NO_2/NO_x$ production; (3), no interference with the oxygen carrying function of hemoglobins since compounds administered herein do not react with heme in hemoglobin, so the physiological level in blood of methemoglobin will be less than 5% in blood; (4), NO bioactivity is preserved when the compound administered reacts with cysteine of hemoglobin; (5), is more efficient and selective at loading hemoglobin cysteine with NO group than free NO or nebulized nitric oxide-releasing compound liquid or solid; (6), the advantages associated with administration of a gas including matching to blood perfusion (ideal distribution), relatively localized lung effect compared to normal systemic administration of solutions and familiarity of anesthesiologists with the procedure whereby the administration is carried out. The method preserves the advantages of both NO gas inhalation and nebulized nitric oxide-releasing compound administration while minimizing the disadvantages associated with these known methods.

As used herein the term $NO_x$ means NO, $N_2O_3$, $N_2O_4$, $OONO^-$, OONO. and any products of their interaction or their reaction with NO or $NO_2$.

As used herein the term reactive oxygen species is singlet oxygen, superoxide, hydrogen peroxide or hydroxyl radical.

As used herein the term hypoxemia means low blood oxygen content compared to normal, i.e., a hemoglobin saturation less than 95% and a $Pa_{O2}$ less than 90 in arterial blood in someone breathing room air.

As used herein the term $Pa_{O2}$ means the partial pressure of oxygen in gases in arterial blood.

DETAILED DESCRIPTION OF THE INVENTION

Figure 1:
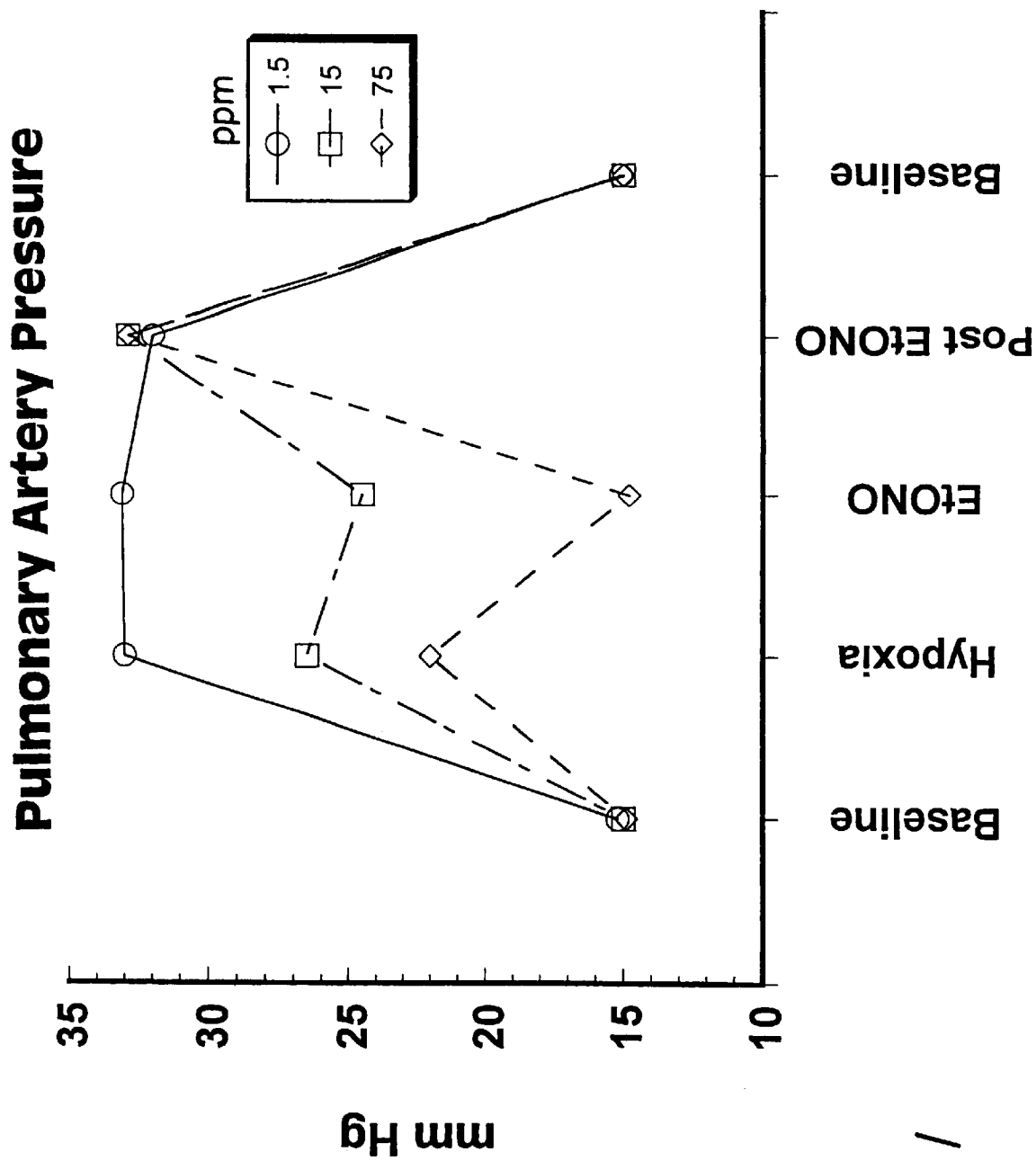
FIG. 1 depicts graphs of pulmonary artery pressure for three doses of ethyl nitrite gas and shows results of Example I.

We turn now to the method for treating a pulmonary disorder associated with smooth muscle constriction in lungs and/or hypoxemia in a patient having such disorder, said method comprising delivering into the lungs of said patient as a gas, a therapeutically effective amount of a compound having an NO group and having a hypoxemia relieving effect and a smooth muscle constriction relieving effect with said NO group being bound in said compound so it does not form $NO_2$ or $NO_x$ in the presence of oxygen or reactive oxygen species at body temperature.

The pulmonary disorders treatable by this method include, for example, pulmonary hypertension, acute respiratory distress syndrome (ARDS), asthma and cystic fibrosis.

Pulmonary hypertension is associated with smooth muscle constriction in the lungs and it can be associated with hypoxemia.

ARDS is a radiographic manifestation associated with low oxygen content in blood and typically is also associated with elevated pulmonary pressures. Oxygen free radical injury contributes to the pathophysiology. Free NO can aggravate the injury by reacting with oxygen free radicals to form toxic products of reaction (i.e., they damage tissues), but the compounds administered herein do not have this effect because they do not react with oxygen free radicals. This disorder is associated with hypoxemia and it can be associated with smooth muscle constriction in the lungs.

Asthma is associated with smooth muscle constriction in the lungs and can be associated with hypoxemia.

Cystic fibrosis is associated with smooth muscle constriction in the lungs and can be associated with hypoxemia.

We turn now to the compounds having an NO group and having a hypoxemia relieving and a smooth muscle constriction relieving effect with said NO group being bound in said compound. These compounds are less reactive with oxygen or with oxygen free radicals at body temperature than NO and are more potent antimicrobials than NO. These compounds include, for example, those having the formula $X-NO_y$ where X is an oxygen, sulfur, nitrogen or metal selected, for example, from the group consisting of iron, copper, ruthenium and cobalt atoms or an alkyl or alkenyl or alkylthio or alkenylthio group containing from 1 to 6 carbon atoms which is straight chain or branched, $CF_3-$ and $CF_3S-$, and y is 1 or 2, provided that when x is oxygen, y is 2.

Specific treating agents for use herein include, for example, ethyl nitrite (which is used in examples herein), methyl nitrite, tert-butyl nitrite, isoamyl nitrite, trifluoronitrosomethane ($CF_3NO$), $CF_3SNO$, $CH_3SNO$, $CH_2=CHSNO$, $CH_2=CHCH_2SNO$, $ONSCH_2-CH_2-CH_2SNO$ and $CH_3CH_2CH_2SNO$. Alkyl nitrites can be prepared as described in Landscheidt et al. U. S. Pat. No. 5,412,147. Ethyl nitrite is available commercially, e.g., diluted in ethanol. $CF_3NO$ is a commercial product or can be made by treatment of $CF_3I$ with $NO^-$ as described in J. Phys. Chem 100, 10641 (1996). Aliphatic thionitrites, i.e., compounds of the form RSNO where R describes an alkyl or alkenyl moiety, can be prepared by treatment of the corresponding thiol with a source of $NO^+$ including, but not limited to, one or more of the following: tert-butyl nitrite, ethyl nitrite, nitrosonium tetrafluoborate ($NOBF_4$), nitrosonium perchlorate ($NOClO_4$), nitrosonium hydrogen sulfate ($NOHSO_4$), nitrosonium hydrogen phosphate ($NOH_2PO_4$), or HCl-acidified solutions of sodium nitrite.

We turn now to the administration of these compounds. Those that are normally gases are readily administered diluted in nitrogen or other inert gas and can be administered in admixture with oxygen. Those that are not normally gases are converted to gas for administration and are administered diluted as in the case of the NO-containing compounds that are normally gases. The compounds should not have a boiling point such that the temperature required to maintain them as gases in diluted form would harm the lungs and preferably would not condense in the lungs.

Dilution, for example, to a concentration of 1 to 100 ppm is typically appropriate.

The diluted gas is readily delivered into the lungs, using a ventilator which is a conventional device for administering gases into the lungs of a patient. A tube attached to the device passes the gas into the lungs at a rate and pressure consistent with maintaining a $Pa_{O2}$ of 90 mm Hg. Time periods of administration typically range from 1 minute to two or more days, and administration is carried out until symptoms abate. Administration can also be carried out using a face mask.

As indicated above, a therapeutically effective amount is administered. This is a hypoxemia relieving effective and smooth muscle constriction relieving effective amount. Administration is carried out for as long as symptoms ameliorate.

Ethyl nitrite is readily delivered to the patient in gaseous form by bubbling $N_2$ or $O_2$ through a Mlligan gas diffuser containing ethyl nitrite diluted in ethanol, e.g., at a flow rate of 0.5 ml/min, to produce $N_2$ or $O_2$ containing ethyl nitrite and introducing this into the ventilation system by mixing the output from the ventilator with the $N_2$ or $O_2$ containing ethyl nitrite, for example, to produce a concentration of 1 to 100 ppm ethyl nitrite in the resulting gas, and delivering this to the patient at a rate and pressure to maintain $Pa_{O2}$ at 90 mm Hg. The concentration of ethyl nitrite gas administered is proportional to the flow rate of $N_2$ or $O_2$ and the concentration of ethyl nitrite liquid in ethanol.

We turn now to the method for treating a cardiac disorder which is characterized by ischemia, pump failure and/or afterload increase in a patient having such disorder, said method comprising delivering into the lungs of said patient as a gas, a therapeutically effective amount of a compound which reacts with cysteine in hemoglobin and/or dissolves in blood and has an NO group which is bound in said compound so it does not form $NO_2$ or $NO_x$ in the presence of oxygen or reactive oxygen species at body temperature.

The cardiac disorders treatable by this method include angina, myocardial infarction, heart failure and hypertension.

In the case of treating hypertension, it is required that the NO-group containing compound administered is one that reacts with cysteine in hemoglobin, e.g., ethyl nitrite discussed ii below, and that a thiol also be administered systemically or by inhaled route to promote systemic release of NO from binding to cysteine of hemoglobin. In the cases of treating other cardiac disorders, where the NO-containing compound administered is one that reacts with cysteine in hemoglobin, e.g., ethyl nitrite discussed below, it is an option that a thiol also be administered systemically or by inhaled route to cause systemic release of NO from binding to cysteine of hemoglobin. Suitable thiols include, for example, N-acetylcysteine (dosage, e.g., ranging from 50 to 200 mg/kg with preferred route of administration being intravenous or nebulized), glutathione (dosage, e.g., ranging from 50 to 200 mg/kg with preferred route of administration being intravenous), and cysteinylglycine (dosage, e.g., ranging from 50 to 200 mg/kg with preferred route of administration being intravenous).

We turn now to the compounds which react with cysteine in hemoglobin and/or dissolve in blood and have an NO group which is bound in said compounds so it does not form $NO_2$ or $NO_x$ in the presence of oxygen or reactive oxygen species at body temperature, for use in the method herein for treating cardiac disorders. These compounds include, for example, those having the formula $X—NO_y$ described above and the species of this class recited above (ethyl nitrite is used in working examples hereinafter); as indicated above, those compounds that are not normally gases, i.e., not gases at room and body temperature, are converted to gas for administration.

The concentrations of NO-containing compound and methods of administration applicable to the method of treating a pulmonary disorder described above are applicable to the method herein for treating cardiac disorders.

As indicated above, a therapeutically effective amount of NO-containing compound in gas form is administered in the method herein for treating cardiac disorders. This is a chest pain reducing effective amount for angina, a heart failure resolving effective amount for myocardial infarction, a pulmonary pressure reducing and peripheral vascular resistance reducing effective amount for heart failure and a blood pressure lowering effective amount for hypertension.

For administration of ethyl nitrite for treating cardiac disorders, the same concentrations and methods of administration are applicable as are described above for treating pulmonary disorders.

We turn now to the method for treating a blood disorder in a patient having said disorder, said method comprising delivering into the lungs of said patient as a gas, a therapeutically effective amount of a compound which reacts with cysteine in hemoglobin and/or dissolves in blood and has an NO group which is bound in said compound so that it does not form $NO_2$ or $NO_x$ in the presence of oxygen or reactive oxygen species at body temperature.

The blood disorders are those ameliorated by treatment with NO or related molecules, i.e., where NO would change the shape of red blood cells to normal or restore their function to normal or would cause dissolution of blood clots. These include sickle cell disease and clotting disorders including disseminated intravascular coagulation (DIC), heart attack, stroke, and Coumadin induced clotting caused by Coumadin blocking protein C and protein S.

We turn now to the compounds which react with cysteine in hemoglobin and/or dissolve in blood and have an NO group which is bound in said compound so that it does not form $NO_2$ or $NO_x$ in the presence of oxygen or reactive oxygen species at body temperature, for use in the method herein for treating blood disorders. These compounds are the same as those recited for treating cardiac disorders and include, for example, those having the formula $X—NO_y$ described above and the species of this class recited above; as indicated above, those compounds that are not normally gases, are converted to gas form for administration.

The concentrations of NO-containing compound and methods of administration applicable to the method for treating a pulmonary disorder described above are applicable to the method herein for treating blood disorders.

As indicated above, a therapeutically effective amount of NO-containing compound in gas form is administered in the method herein for treating blood disorders. This is a red blood cell shape restoring and/or red blood cell function restoring effective amount for sickle cell disease and a clot dissolving and/or clot formation preventing amount for clotting disorders.

Where the NO-group containing compound administered for treating a blood disorder is one that reacts with cysteine in hemoglobin, it is advantageous to administer the NO-group containing compound in conjunction with a thiol to cause systemic release of NO from binding to cysteine of hemoglobin. Suitable thiols, dosages and routes of administration are those described in conjunction with thiols above.

For administration of ethyl nitrite for treating cardiac disorders, the same concentrations and methods of administration are applicable as are described above for treating pulmonary disorders.

The invention herein is illustrated by, but not limited by, the following working examples.

EXAMPLE I

The experiment was carried out using a pig model of pulmonary hypertension as follows:

Mixed strain two-three weeks old piglets were utilized. Initial anesthetic induction was by inhaled halomethane 5%, reduced to 2% when the animal was stable. A bolus of 20 µg/kg of fentanyl and 0.2 mg/kg of acepromazine was given after tracheostomy surgery and insertion of a jugular venous line, followed by a continuous fentanyl infusion of 10 µg/kg/hr. An incision in the right side of the neck allowed the insertion of a catheter through the external jugular vein into the right atrium, through which maintenance i.v. fluid of 30 mL/kg/hr of 5% glucose was infused. A catheter was placed in the carotid artery for measurement of systolic arterial pressure (SAP). After the tracheostomy, halothane was discontinued, assisted ventilation was started, and paralysis was obtained using pancuronium bromide (0.1 mg/kg) every 45 minutes. Further bolus doses of fentanyl (5–10 µg/kg) were administered as necessary. Through a left thoracotomy, a 6- or 8-mm ultrasound flow probe (Transonic Inc., Rochester, N.Y.) was placed around the pulmonary artery for measurement of cardiac output and a 4- to 6-mm probe was placed around the ductus arteriosus. A 22-gauge catheter was inserted into the root of the pulmonary artery through a purse string suture for the continuous measurement of pulmonary artery pressure (PAP). The systemic and pulmonary catheters were connected to pressure transducers and together with the ECG signal, displayed on a neonatal monitor (Model 78833B, Hewlett Packard, Waltham, Mass.). Systemic oxygen saturation ($SaO_2$) was measured using a subcutaneous pulse oximeter (N200, Nellcor Inc., Hayward, Calif.). A continuous infusion of bicarbonate (15 mEq/100 mL of i.v. fluid) was given to prevent severe acidosis during periods of hypoxia. Cardiac output was determined from measurements of the calibrated ultrasonic flow probe.

After this instrumentation, the animal was allowed to rest for 20 minutes to ensure stability, which was defined as less than 5% variation in heart rate, SAP, and PAP over a 5-minute period, and thereafter hypoxia was induced by reduction of the inspired oxygen concentration to 10 to 14% to produce a target $SaO_2$ of 35 to 45%. After induction of hypoxia, a stable hypoxic baseline was obtained (2 minutes). An arterial blood specimen was obtained for the measurement of blood gases and methemoglobin.

Ethyl nitrite (EtONO) was then administered according to a computer-generated random sequence in doses of 1.5, 15 or 75 ppm by changing the EtONO concentration (at a fixed flow rate), maintaining the fractional inspired oxygen saturation ($FiO_2$) at the same level. The ethyl nitrite was administered with nitrogen by introducing nitrogen ethyl nitrite admixture into the ventilation system by mixing the output from the ventilator with said admixture. The ethyl nitrite nitrogen admixture was generated by bubbling nitrogen through a Milligan gas diffuser (Fisher Scientific) containing ethyl nitrite diluted in ethanol at a flow rate of 0.5 ml/min to produce nitrogen containing ethyl nitrite. The concentration of ethyl nitrite in the gas to be administered is directly proportional to the flow of nitrogen into the Milligan gas diffuser and/or the concentration of ethyl nitrite in ethanol. Measurements were obtained at each dose when there were no further changes in PAP, $SaO_2$, SAP, or cardiac output, and the signals were recorded for 1 minute. At this point, EtONO administration was discontinued. Post EtONO data was from samples 4 minutes after EtONO discontinuance and final baseline samples were taken when the parameter being measured stabilized (about 4 minutes after the post EtONO sample). This procedure was repeated until all doses of EtONO had been administered. If an animal experienced significant hypotension (systolic arterial pressure decreasing to less than 60% of hypoxic baseline), the hypoxia was terminated, and the animal was allowed to recover before reintroducing hypoxia.

The physiologic parameters of interest were acquired through a personal computer (Dell 486/33, Dell Computer Corporation, Richmond Hill, Ontario, Canada) using an analog-to-digital converter (DT 2801, Data Translation Inc., Marborough, Mass.). Software for acquisition analysis was written using Asyst Scientific Software System (Macmillan Software Co., New York, N.Y.). With this software, continuous acquisition of the measured parameters was performed for a 2-minute period at baseline, and a 1-minute period after stability during each hypoxic EtONO exposure. The computer-generated averages of the measured parameters were then utilized for subsequent analyses. The time responses of the changes in PAP were similarly analyzed using the average values for 1 second for the PAP to determine the time response of the change in PAP compared to baseline. All signals were acquired at 24 Hz. In order to compensate for sampling delay time for the analyzer which was approximately 5 seconds, initiation of the response was considered to be 5 seconds before the initial indication that the results of the appropriate dose had been measured by the analyzer (measured by GC mass spectral analysis using a model system). Cardiac Index was calculated as cardiac output divided by the animal's weight in kilograms. Pulmonary Vascular Resistance (PVR) was calculated as mean PAP divided by cardiac index. Pulmonary Artery Flow (FIG. 3) was measured using a Doppler flow probe.

Results are shown in FIGS. 1–6.

FIG. 1 depicts graphs of PAP in mm Hg for the three concentrations of EtONO administration with data points at baseline, hypoxia (stable hypoxic baseline), EtONO (when no further changes in PAP for one minute), post EtONO (4 minutes after EtONO discontinuance) and baseline (when PAP normalized, approximately 4 minutes after post EtONO data). The data shows hypoxia increased PAP and that EtONO administration reverses hypoxic pulmonary vasoconstriction.

Figure 2:
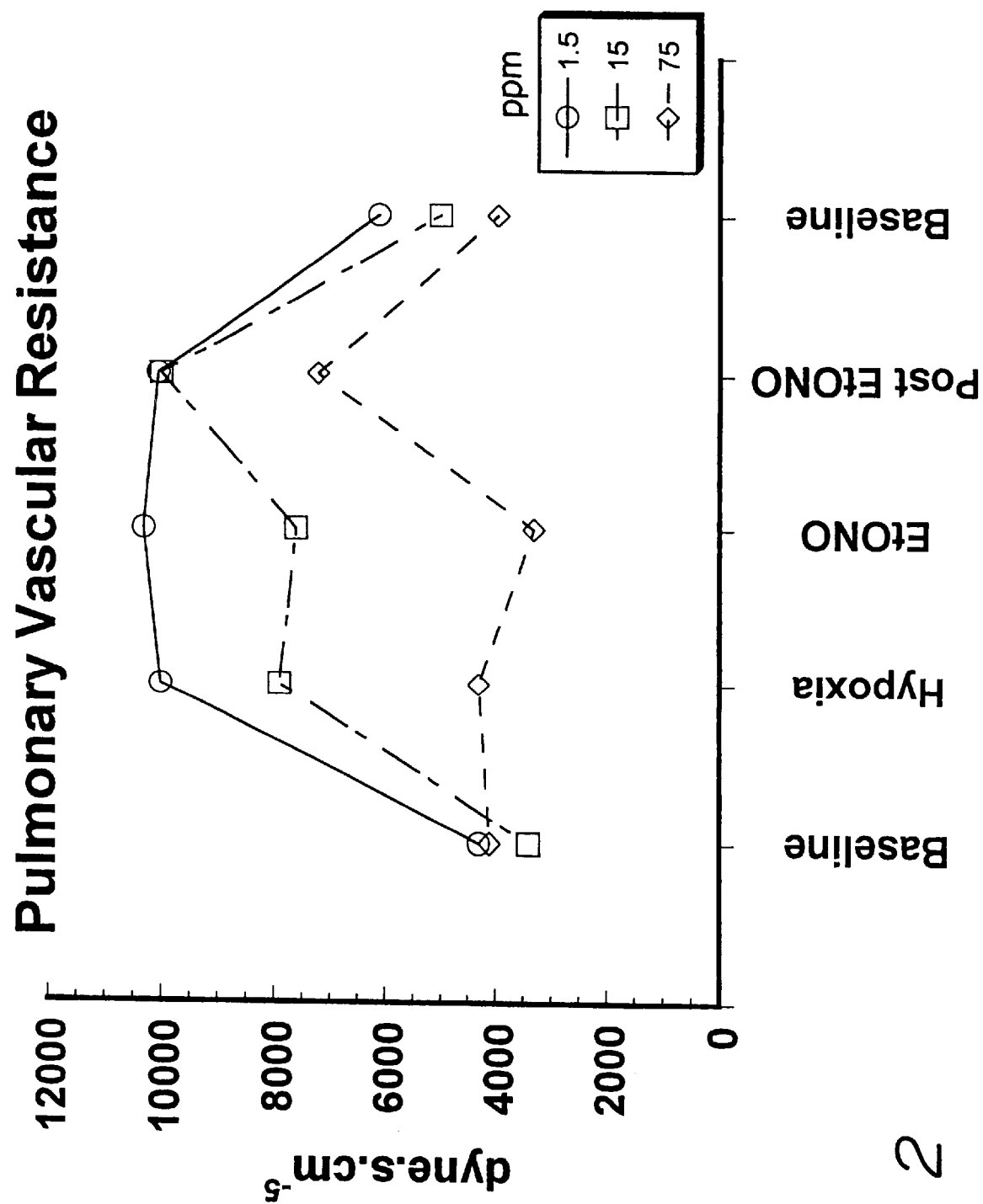
FIG. 2 depicts graphs of pulmonary vascular resistance for three doses of ethyl nitrite gas and shows results of Example I.

FIG. 2 depicts graphs of PVR in $dynes \times 5 \times cm^{-1}$ for the three concentrations of EtONO administration with data points at the same stages as for FIG. 1. The data shows hypoxia increased PVR and that EtONO administration restores PVR toward initial baseline.

Figure 3:
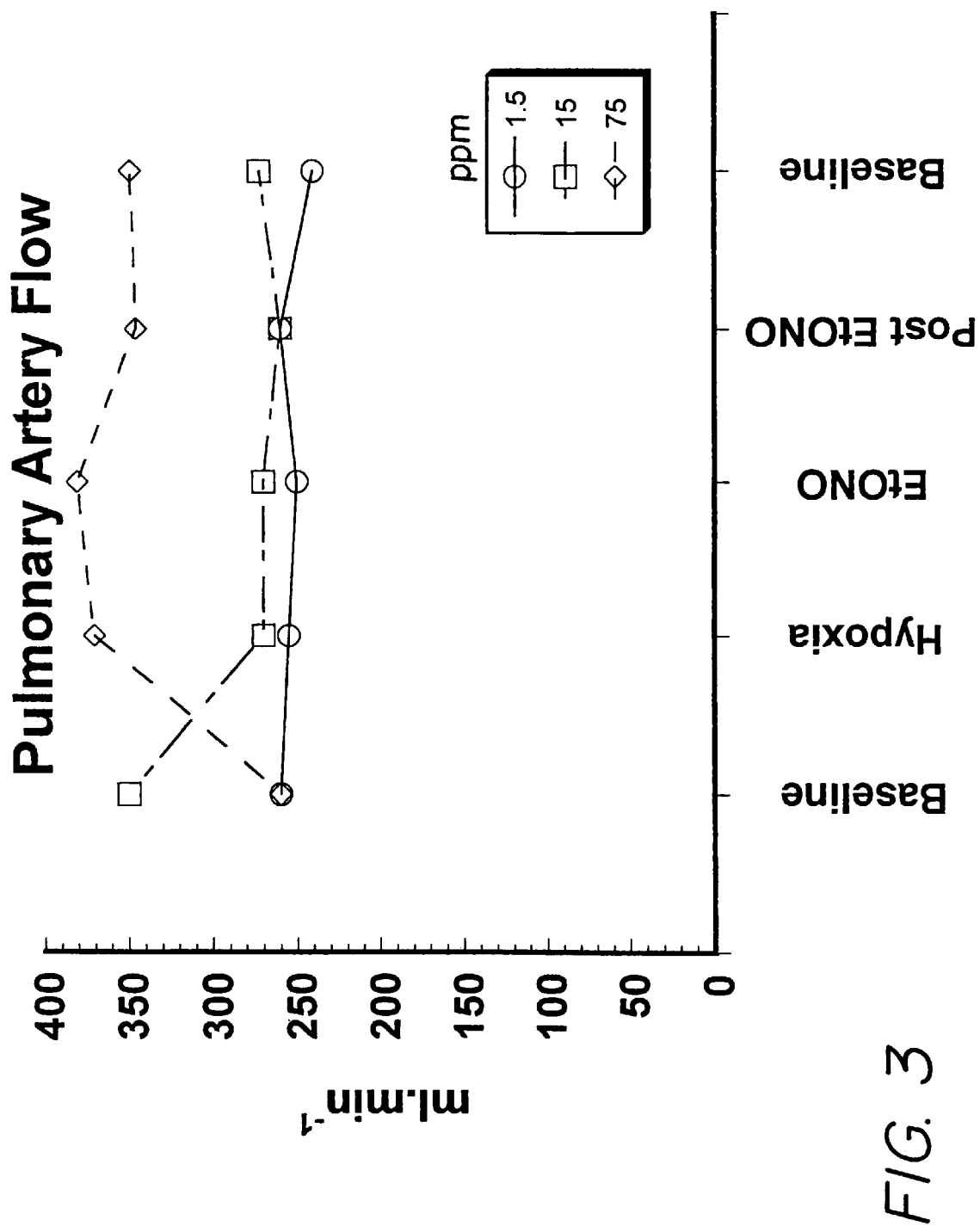
FIG. 3 depicts graphs of pulmonary artery flow for three doses of ethyl nitrite gas and shows results of Example I.
Figure 4:
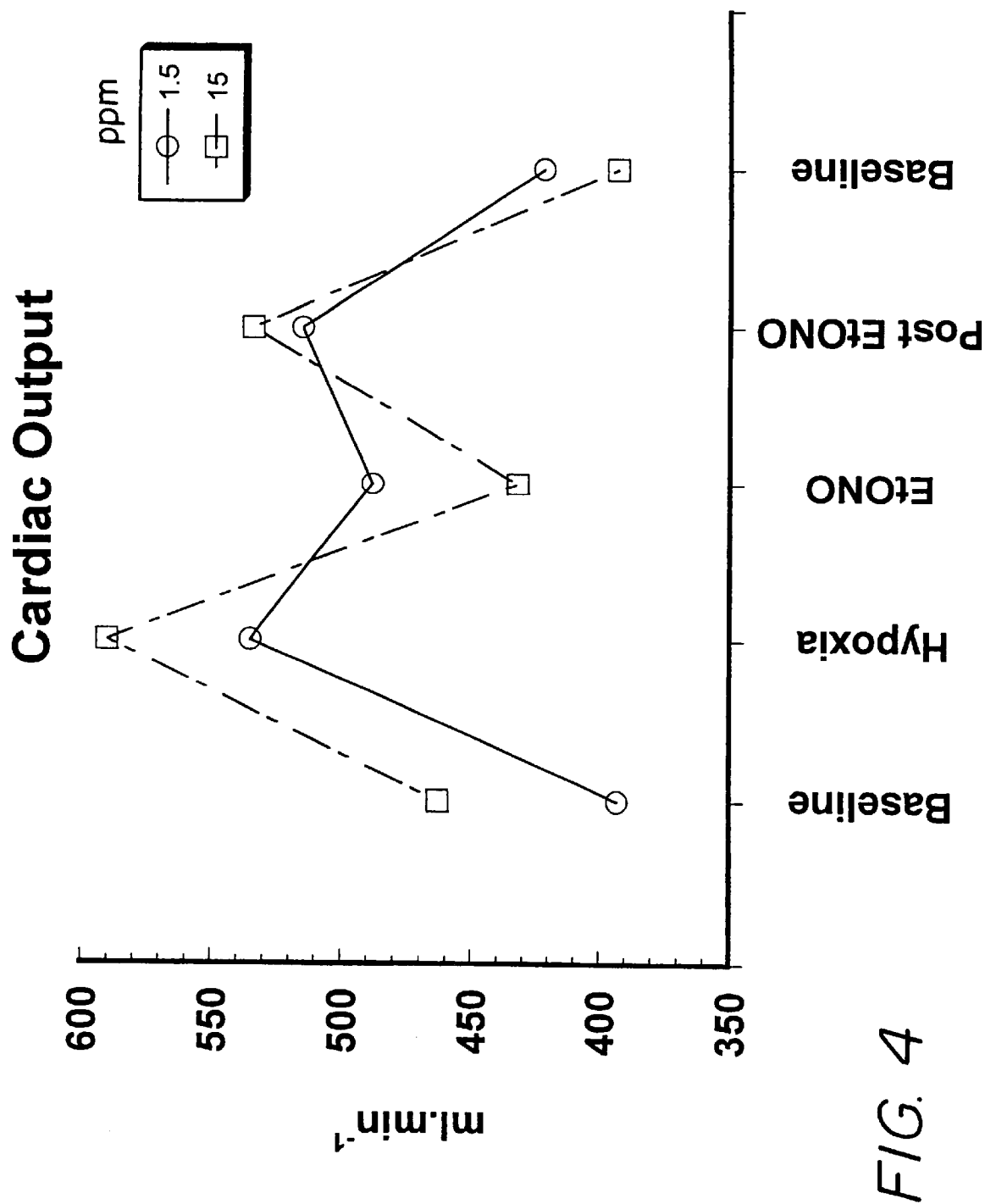
FIG. 4 depicts graphs of cardiac output for two doses of ethyl nitrite gas and shows results of Example I.

FIG. 3 depicts graphs of pulmonary artery flow in ml/min for the three concentrations of EtONO administration with data points at the same stages as for FIG. 1. The data shows EtONO administration increases pulmonary artery flow at 75 ppm FIG. 4 depicts graphs of cardiac output in ml/min for two concentrations of EtONO administration with data points at the same stages as for FIG. 1. The data shows that EtONO administration tends to normalize the hypoxia induced increase in cardiac output.

Figure 5:
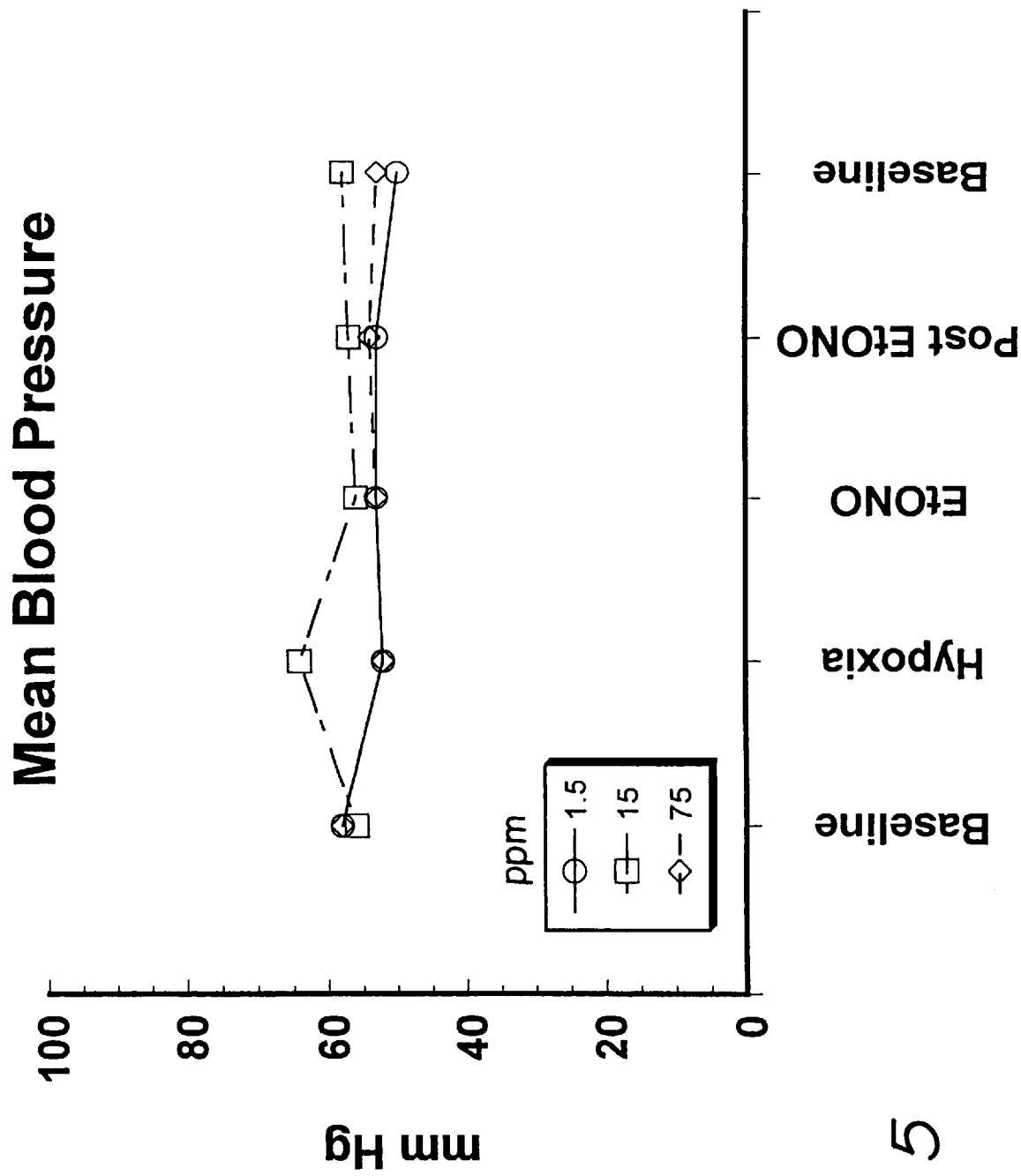
FIG. 5 depicts graphs of mean blood pressure for three doses of ethyl nitrite gas and shows results of Example I.

FIG. 5 depicts graphs of mean blood pressure in mm Hg for three concentrations of EtONO administration with data points at the same stages as for FIG. 1. The data shows that EtONO administration has no effect on blood pressure.

Figure 6:
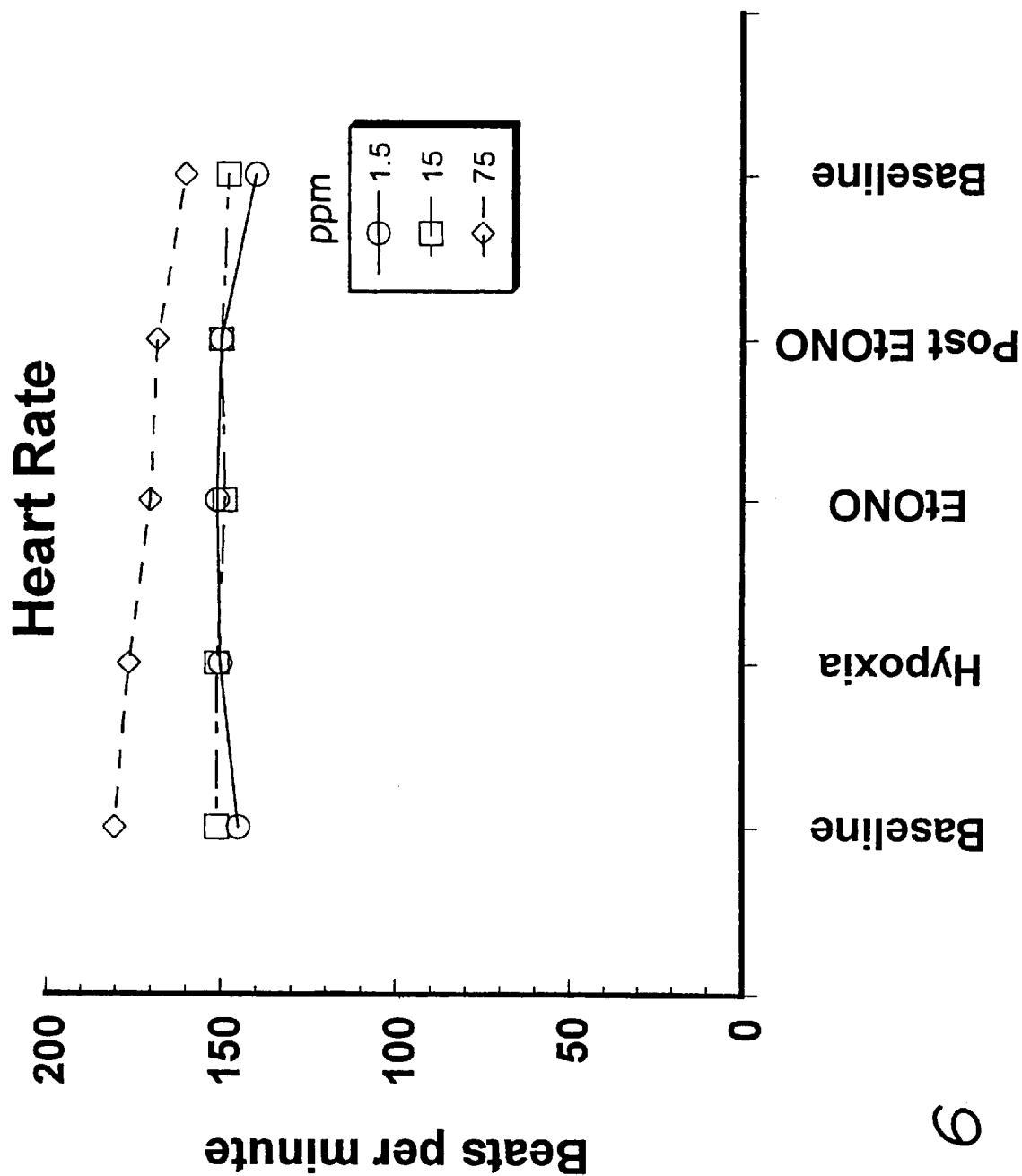
FIG. 6 depicts graphs of heart rate for three doses of ethyl nitrite gas and shows results of Example I.

FIG. 6 depicts graphs of heart rate in beats per minute for three concentrations of EtONO administration with data points at the same stages as for FIG. 1. The data shows that EtONO administration has no effect on heart rate.

Blood samples taken during inhalation of the highest dose of EtONO administered (75 ppm) show methemoglobin content ranging from 0.5 to 4.5% (n=5), i.e., well within the acceptable physiological range.

Figure 7:
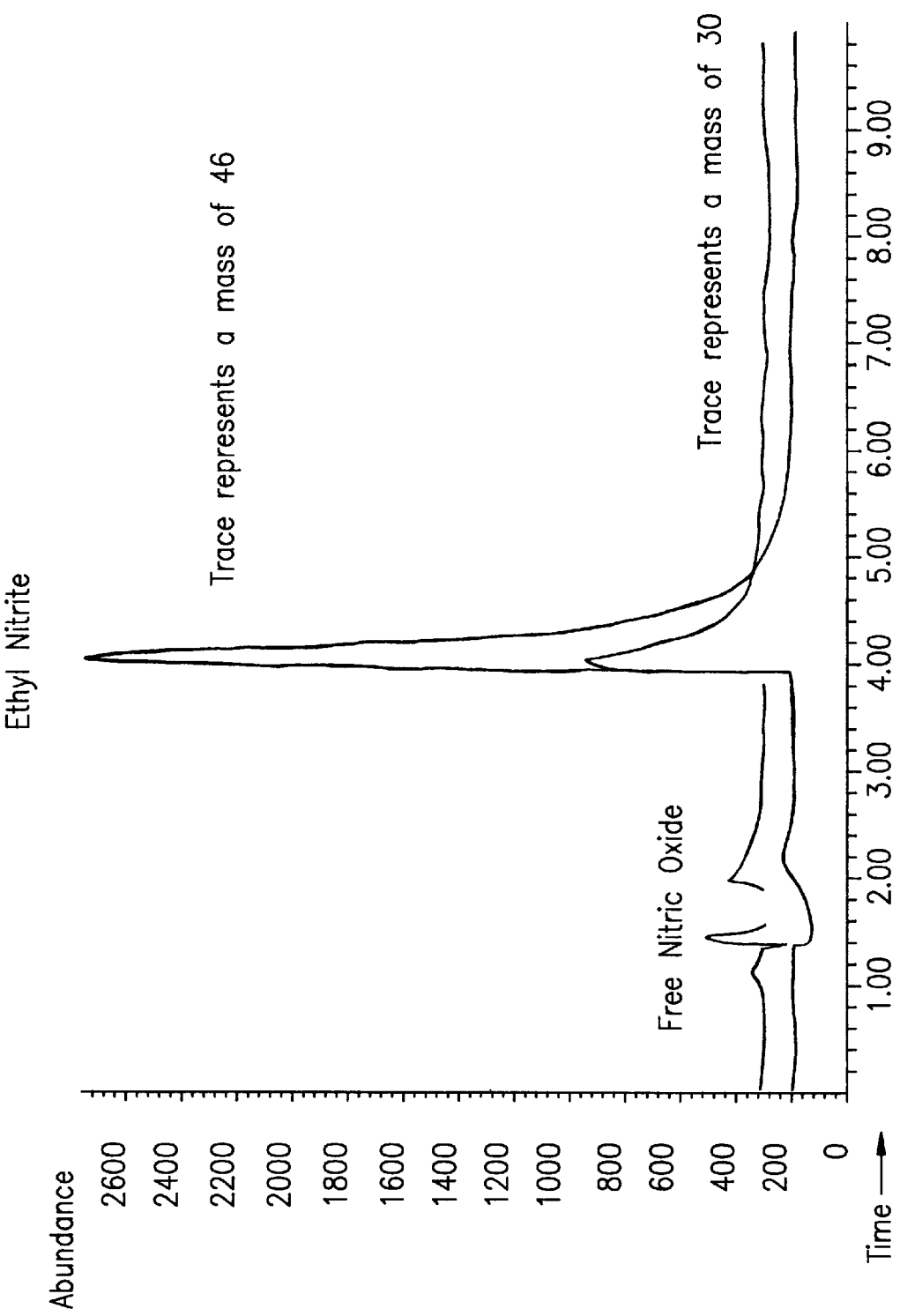
FIG. 7 shows gas chromatography/mass spectral analysis results on ethyl nitrite gas delivered through the ventilation system of Example I at 75 ppm.

Gas chromatography/mass spectrometer analysis on gas delivered on admixture of nitrogen ethyl nitrite admixture with ventilator output, at 75 ppm ethyl nitrite, was carried out. In particular, a 100 $\mu l$ gas sample was taken from the expiratory arm of the respiration system (using a glove as a model lung) with ethyl nitrite being delivered from the system to the patient at 75 ppm. The gas sample was injected into an HP GC/MS system using a 30 m 0.53 $\mu m$ GS-Q column. Ethyl nitrite is decomposed within the mass spectrometer producing ethanol (mass 46) and some NO (mass 30) but virtually no free NO was generated. The results are shown in FIG. 7. Unbound nitric oxide elutes from the GS-Q column at approximately 1.5 minutes and ethyl nitrite elutes from the column at 4.1 minutes. The data shows virtually no free NO or $NO_2$ is detected.

EXAMPLE II

A 30-year-old white female with pulmonary pressures of 70/40 mm Hg is admitted into an intensive care unit and deteriorates due to right heart failure, and is given for inhalation through a face mask an admixture of $O_2$, $N_2$ and ethyl nitrite such that the $Pa_{O2}$ is maintained at 90 and ethyl nitrite is present at 70 ppm Pulmonary pressures fall to 30/15 and right heart failure disappears.

In another case, an identical patient receives the same treatment except for 80 ppm inhaled NO in place of the 70 ppm ethyl nitrite. Pulmonary pressures drop but the patient develops airway hyperreactivity (slight wheezing) and a chemiluminescence analyzer shows threefold increase in $NO_2$ concentration in exhaled air. Moreover, methemoglobin content in the blood is measured at 10%. The patient is switched from NO to inhaled ethyl nitrite (70 ppm), and $NO_2$ and methemoglobin levels drop and recovery is maintained.

Example III

A 60-year old male cancer patient develops radiographic changes consistent with ARDS, post-chemotherapy. The patient's $Pa_{O2}$ falls to 50 mm Hg despite being on 100% oxygen and a right heart catheterization reveals a normal left ventricular endiastolic pressure. The patient is administered 40 ppm inhaled ethyl nitrite. The $Pa_{O2}$ increases to 70 mm Hg.

An identical patient is given 30 ppm inhaled NO and acute $Pa_{O2}$ improvement occurs but then clinical deterioration occurs characterized by worsening chest X-rays (due to inflammation) and $Pa_{O2}$ drops from 70 to 60 mm Hg. The patent is switched to 50 ppm inhaled ethyl nitrite and the radiographic changes stabilize and $Pa_{O2}$ increases to 90 mm Hg.

EXAMPLE IV

A 26-year old white female asthmatic gets intubated because of a severe asthmatic exacerbation. The patient is administered nebulized epinephrine and Atrovent but is failing to ventilate. The physician adds 100 ppm inhaled ethyl nitrite to the treatment, and the patient's $Pa_{O2}$ improves from 60 to 80 and ventilation becomes easier as evidenced by lower airway pressures.

EXAMPLE V

A 12-year old girl with cystic fibrosis presents with pseudomonal infection leading to pulmonary exacerbation. The patient is given nebulized antibiotics but continues to spike fever and do poorly. Inhaled ethyl nitrite is given at 80 ppm with resolution of the infection over four days.

EXAMPLE VI

A 65-year old white male is admitted to a hospital with unstable angina. The patient is given i.v. nitroglycerin, heparin and a beta blocker. However, the patient continues to experience intermittent chest pain at rest. The patient is given 60 ppm inhaled ethyl nitrite. The chest pain resolves.

EXAMPLE VII

A 70-year old white male presents with myocardial infarction. The patient's hematocrit is 26. The patient is given two units of blood but goes into heart failure. The patient is started on 60 ppm inhaled ethyl nitrite, with resolution of the heart failure. The patient also receives the standard medical regimen of tissue plasminogen activator, a beta blocker and an ACE inhibitor.

EXAMPLE VII

An 80-year old presents with stage 3 biventricular failure and pulmonary arterial pressures of 50/30. The patient is given Captopril, digoxin and lasix but still has a systemic pressure of 140/80 with increased vascular resistance. The patient receives 80 ppm inhaled ethyl nitrite gas. The patient's pulmonary pressures drop to 20/10 and systemic arterial pressure drops to 100/80 with normal peripheral vascular resistance.

EXAMPLE IX

A 40-year old black male presents with malignant hypertension (blood pressure of 240/160). The patient receives Captopril and nitroprusside and blood pressure drops to 200/120. The patient receives 80 ppm inhaled ethyl nitrite over the next day with an intravenous bolus of 200 mg/kg N-acetylcysteine administered at 6 hours after ethyl nitrite therapy was started. Blood pressure drops to 170/95.

EXAMPLE X

An 18-year old black female with homozygous sickle cell disease presents in crisis. The patient complains of severe abdominal and chest pain and is somewhat disoriented. She receives two units of blood while being administered 80 ppm inhaled ethyl nitrite. All symptoms resolve.

EXAMPLE XI

A 60-year old white male with leukemia presents with disseminated intravascular coagulation. A digit becomes ischemic. The patient is started on 80 ppm inhaled ethyl nitrite and is given 100 mg/kg infusion of N-acetylcysteine. Blood flow improves to the digit.

Variations

Variations of the above will be obvious to those skilled in the art. Thus, the scope of the invention is defined by the claims.

What is claimed is:

1. A method for treating a pulmonary disorder associated with hypoxemia or smooth muscle constriction or hypoxemia and smooth muscle constriction in a patient having such disorder, said method comprising the step of delivering into the lungs of said patient as a gas, a therapeutically effective amount of a compound having an NO group and having a hypoxemia relieving and smooth muscle constriction relieving effect with said NO group being bound in said compound so that it does not form $NO_2$ or $NO_x$ in the presence of oxygen or reactive oxygen species at body temperature.

2. The method of claim 1 wherein the compound is ethyl nitrite.

3. The method of claim 2 where the disorder is pulmonary hypertension.

4. The method of claim 2 where the disorder is acute respiratory distress syndrome.

5. The method of claim 2 where the disorder is asthma.

6. The method of claim 2 where the disorder is cystic fibrosis.

7. The method of claim 1 where the disorder is pulmonary hypertension.

8. The method of claim 1 where the disorder is acute respiratory distress syndrome.

9. The method of claim 1 where the disorder is asthma.

10. The method of claim 1 where the disorder is cystic fibrosis.

11. A method for treating a cardiac disorder which is characterized by ischemia or heart failure or afterload increase or ischemia and heart failure or ischemia and afterload increase or heart failure and afterload increase or ischemia and heart failure and afterload increase in a patient having such disorder, said method comprising the step of delivering into the lungs of said patient as a gas, a therapeutically effective amount of compound which dissolves in blood and has an NO group which is bound in said compound so that it does not form $NO_2$ or $NO_x$ in the presence of oxygen or reactive oxygen species at body temperature.

12. The method of claim 11 where the disorder is angina.

13. The method of claim 11 where the disorder is myocardial infarction.

14. The method of claim 11 where the disorder is heart failure.

15. The method of claim 11 where said compound reacts with cysteine in hemoglobin.

16. The method of claim 15 where the disorder is hypertension and where thiol is administered systemically or by inhaled route to cause systemic release of NO from binding to cysteine of hemoglobin.

17. The method of claim 11 wherein said compound is ethyl nitrite.

18. A method for treating a blood disorder which is ameliorated by treatment with NO in a patient having said disorder, said method comprising the step of delivering into the lungs of said patient as a gas, a therapeutically effective amount of a compound which dissolves in blood and has an NO group which is bound in said compound so that it does not form $NO_2$ or $NO_x$ in the presence of oxygen or reactive oxygen species at body temperature.

19. The method of claim 18 where the disorder is sickle cell disease.

20. The method of claim 18 where the disorder is a clotting disorder.

21. The method of claim 18 where the compound is ethyl nitrite.

22. The method of claim 18 where said compound reacts with cysteine in hemoglobin.

* * * * *